US009901090B2

(12) United States Patent
Kelly

(10) Patent No.: US 9,901,090 B2
(45) Date of Patent: Feb. 27, 2018

(54) PESTS AND BIOLOGICAL AEROSOL DETECTION DEVICES

(71) Applicant: Sean Kelly, Yorba Linda, CA (US)

(72) Inventor: Sean Kelly, Yorba Linda, CA (US)

( * ) Notice: Subject to any disclaimer, the term of this patent is extended or adjusted under 35 U.S.C. 154(b) by 176 days.

(21) Appl. No.: 14/845,229

(22) Filed: Sep. 3, 2015

(65) Prior Publication Data

US 2017/0064942 A1    Mar. 9, 2017

Related U.S. Application Data

(60) Provisional application No. 62/046,155, filed on Sep. 4, 2014.

(51) Int. Cl.
| | | |
|---|---|---|
| *A01M 31/00* | (2006.01) | |
| *G01N 33/00* | (2006.01) | |
| *A01M 1/02* | (2006.01) | |
| *A01M 1/14* | (2006.01) | |
| *G01N 1/22* | (2006.01) | |

(52) U.S. Cl.
CPC .......... *A01M 31/002* (2013.01); *A01M 1/026* (2013.01); *A01M 1/14* (2013.01); *G01N 1/2202* (2013.01); *G01N 33/0009* (2013.01); *G01N 2001/2223* (2013.01)

(58) Field of Classification Search
CPC ......... A45D 37/00; A61L 9/00; B05B 11/048; B05B 11/043; B05B 11/068; B65D 83/0055; B65D 1/32
See application file for complete search history.

(56) References Cited

U.S. PATENT DOCUMENTS

| | | | | |
|---|---|---|---|---|
| 4,869,407 A | * | 9/1989 | Booth, Jr. ................. | A61L 9/12 206/461 |
| 6,254,836 B1 | * | 7/2001 | Fry ......................... | A61L 9/042 239/211 |
| 6,460,781 B1 | * | 10/2002 | Garcia .................... | A45D 37/00 222/107 |
| 6,536,635 B1 | * | 3/2003 | Garcia .................... | A45D 37/00 222/212 |
| 6,663,019 B2 | * | 12/2003 | Garcia .................... | A45D 37/00 222/630 |
| 6,783,035 B2 | * | 8/2004 | Garcia ............... | B65D 83/0055 222/187 |
| 7,087,552 B2 | * | 8/2006 | Blowers .................. | A01N 3/00 504/114 |
| 7,255,506 B2 | * | 8/2007 | Gruenbacher ......... | A01N 25/34 15/227 |
| 9,138,502 B2 | * | 9/2015 | Irvin ........................ | A61L 9/12 |
| 9,610,375 B2 | * | 4/2017 | Zhang ...................... | A61L 9/12 |
| 2002/0017310 A1 | * | 2/2002 | Gruenbacher ......... | A01N 25/34 132/320 |

(Continued)

*Primary Examiner* — David A Rogers

(74) *Attorney, Agent, or Firm* — James J. Wong

(57) ABSTRACT

The present disclosure provides a device for detecting the presence of insects and bioaerosols comprising, a base and a shell, where the shell is affixed to the base forming a chamber, wherein an agent is contained with said chamber, and at least one channel, the channel(s) provides access to the chamber, the shell can be actuated by a person causing the device to expel air and optionally one or more agents from the chamber to the exterior and to draw in air and bioaerosols from the exterior into the chamber.

8 Claims, 15 Drawing Sheets

(56) References Cited

U.S. PATENT DOCUMENTS

2004/0188461 A1\* 9/2004 Pennaneac'h .......... A45D 34/02
                                                    222/103
2009/0266909 A1\* 10/2009 Ligny .................... A45D 34/02
                                                    239/34

\* cited by examiner

PESTS AND BIOLOGICAL AEROSOL DETECTION DEVICES

CROSS-REFERENCES TO RELATED APPLICATIONS

Not applicable.

STATEMENTS AS TO THE RIGHTS TO INVENTIONS MADE UNDER FEDERALLY SPONSORED RESEARCH OR DEVELOPMENT

Not applicable.

REFERENCE TO A "SEQUENCE LISTING," A TABLE, OR A COMPUTER PROGRAM LISTING APPENDIX SUBMITTED ON A COMPACT DISK

Not applicable.

BACKGROUND OF THE INVENTION

Insects, in general, seem to have a special antagonistic relationship with the psyche of people, this is especially so with insects whose preferred habitats are human living spaces. Insects, such as bed bugs, lice, fleas, and mites, in particular, can pose a threat to the physical and psychological health and well being of people.

The common bed bug, *Cimex lectularius*, is a well known and notorious parasite that feeds on human blood. The bed bug had been relegated to the realm of jokes and stories of a by-gone era. However in the last decade or the so, the pest has staged a comeback due to factors, such as, developed pesticide resistance and increased international travel, which has aided in its propagation and spread.

While bed bugs are not known at this time to transmit any pathogens, there are a number of adverse health effects that may result from bed bug bites, including skin rashes and allergic reactions. And last, but certainly not least, the negative connotation attached with bed bug infestations, which can have drastic economic effects on businesses and cities affected.

Another health concern is biological aerosols, also known as bioaerosols. Bioaerosols are particulate matter of microbial, plant or animal origin. Bioaerosols are sometimes referred to as organic dust, and may consist of pathogenic or non-pathogenic, live or dead bacteria and fungi, viruses, high molecular weight allergens, bacterial endotoxins, mycotoxins, peptide-glycans, beta(1-3)-glucans, pollen, plant fibers, etc. Exposure to bioaerosols is associated with a number diseases such as, infectious diseases and respiratory diseases. Other diseases and conditions have been linked to bioaerosol exposure, such as cancer, pre-term or late term abortions, etc. (Bioaerosol Health Effects and Exposure Assessment: Progress and Prospects, J. Douwes, P. Thorne, N. Pearce and D Heederik, Institute for Risk Assessment Sciences, Division of Environmental and Occupational Health, Utrecht University, The Netherlands; Centre for Public Health Research, Massey University Wellington Campus, Wellington, New Zealand; University of Iowa College of Public Health, Department of Occupational and Environmental Health, IA, USA.)

While seemingly different health concerns, the aforementioned insect pests and bioaerosol share one important common element—detection. In both instances before any remedial or eradication measures can be taken, the degree and type of threat has to be first ascertained. The task of identification is exacerbated by the minute size of the insect pests. Bed bugs, lice, fleas, ticks, and mite are noted for their exceedingly small size, making visual detection challenging. And as discussed previously, bioaerosols are particulate matter that varies from being very small to microscopic. As such there is a need for efficiently and accurately identifying the presence of these threats to humans. The present disclosure addresses these needs and others.

BRIEF SUMMARY OF THE INVENTION

The present disclosure provides a device for detecting the presence of insects and bioaerosols comprising, a base and a shell, where the shell is affixed to the base forming a chamber, wherein an agent is contained with said chamber, and at least one channel, the channel(s) provides access to the chamber, the shell can be actuated by a person causing the device to expel air and optionally one or more agents from the chamber to the exterior and to draw in air and bioaerosols from the exterior into the chamber.

DETAILED DESCRIPTION OF THE INVENTION

Figure 1:
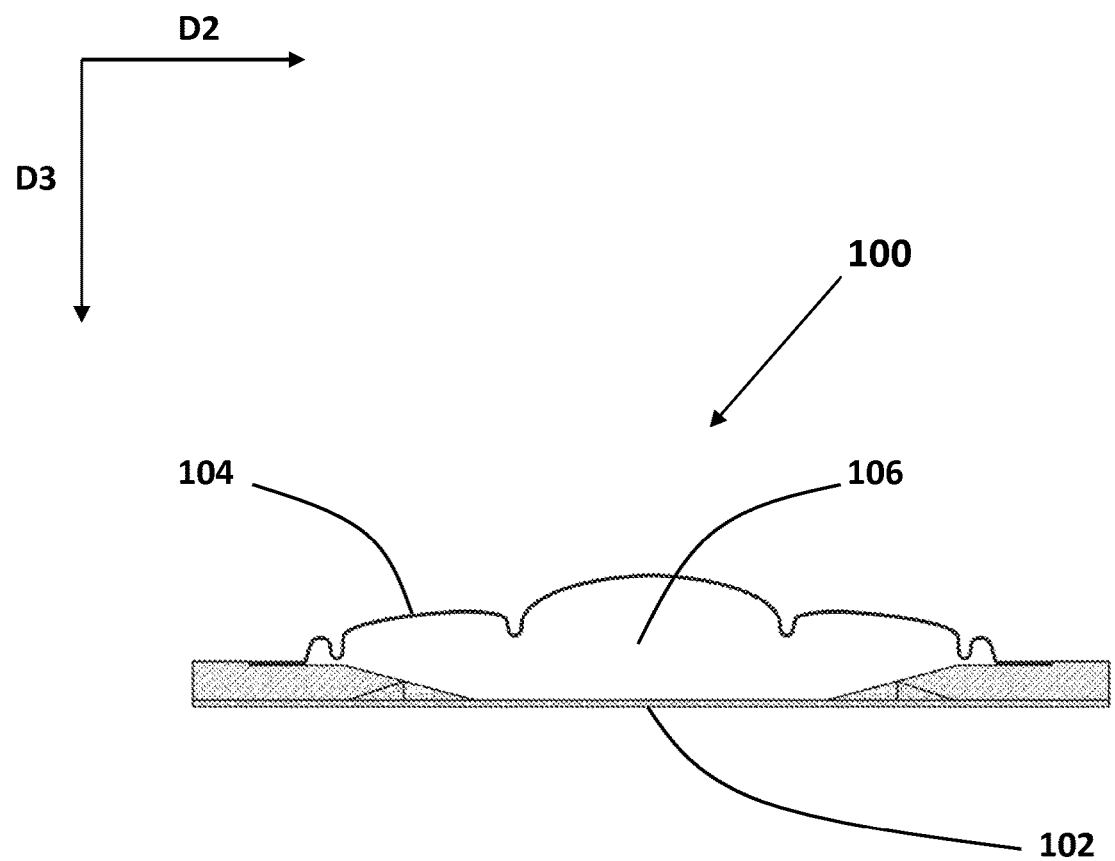
FIG. 1 depicts an embodiment of the present disclosure.

An embodiment of the present disclosure provides a device for detecting the presence of insects and bioaerosols comprising a base and a shell, wherein the shell is made from a form resilient material. The shell is affixed to the base forming a chamber and one or more channels where the channels provide access to the chamber. The openings to the channels may be of a varying size or a uniform size depending upon the desired function at each opening location.

As used herein the term "form resilient" or "form resilience" refers to the quality where a material can deform when a force is applied to it, and then return to its original position when the force is removed. The shell made from form resilient material of the present disclosure provides a flexible structure whose supporting attachments are substantially upon its periphery so as to enable and encourage centralized flexure when acted upon by a force. When the external force is removed, the flexure of such a structure would rebound due to tensile forces inherent in the material.

The terms "biological aerosol", "bioaerosol" or "bioaerosols" refers to living organisms and/or particles of biological origin (microbial, plant or animal) suspended in the air. Bioaerosols may include pollen, mold, bacteria, fungi (including spores and fragments of fungi), viruses, microbial toxin, and the wastes from insect pests, such as dust mite feces.

Another aspect of the present embodiment provides a device having one or more of the openings shaped or sized to achieve the optimum expulsion characteristics of an aerosol such as an air freshener.

Another aspect of the present embodiment provides a device one or more openings shaped or sized to achieve the optimum intake of certain bioaerosols from the surrounding environment.

An aspect of the present embodiment provides a device where the base is made of two layers laminated, that is glued together.

An aspect of the present embodiment provides a device where the base is made with an integral, that is, a seamless base of embossed or injection-molded material.

An aspect of the present embodiment provides a device where the underside of the base is coated with a contact adhesive, or has a magnet, hook and loop, that is, Velcro® or other structure for holding the device against a horizontal, inclined, vertical or inverted surface.

An aspect of the present embodiment provides a device having a low profile. As used herein the term "low profile" refers to an aspect ratio where the depth of the device to the width of the device can range from about 0.25 to 1; 0.3 to 1; 0.4 to 1; 0.5 to 1; 0.6 to 1; and 0.7 to 1. The ratio of the width of the device to the length of the device can range from about 1 to 1 (a substantially circular shape); 1 to 1.2; 1 to 1.3; 1 to 1.4; 1 to 1.5; 1 to 1.6; 1 to 1.7; 1 to 1.8; 1 to 1.9; 1 to 2; 1 to 3; 1 to 4; 1 to 5; or 1 to 6. The dimensions of the disclosed embodiments can be varied to either increase or decrease the amount of air that sampled; and to optimize targeted insects or bioaerosols.

An aspect of the present embodiment provides a device having one or more openings shaped or sized to induce the voluntary entry of a crawling arthropod such as bed bugs. The openings are optionally sized as to draw on or trigger the thigmotropic behavior of arthropods, that is arthropods whose presence is being monitored. As used herein, the term "thigmotropic" or "thigmotropism" refers to the tendency of certain arthropods to prefer spaces in which their bodies experience friction.

The present disclosure provides a insect and bioaerosol detection device useful for detecting insect pests, such as bed bugs, fleas, ants, lice, dust mites and mice and other arthropods pests; and bioaerol, the device comprising a base and a shell, wherein said base is affixed to said shell forming a chamber and one or more channels, wherein said channels provide access to said chamber. In addition to the access of crawling arthropods, such as, insects and spiders, evidence of such arthropods or larger pests such as, mice and other rodents, may be drawn in through the channels. The detection of animal pests, such as mice and rodents can be determined by retaining their dander, feces or hair, which is specific to the particular species. The detection is made by collecting circumstantial evidence, that is, trace materials that could only be present if the pest to which the evidence is associated, was present. This same methodology applies to certain insect pests. For example, the presence of dust mites can be determined by retaining samples of dust mite feces.

An aspect of the present embodiment further comprising a chemical agent is placed in the chamber, wherein the chemical agent attracts certain insects into the device.

Another embodiment of the present disclosure provides a device for detecting the presence of pests particularly bed bugs (Cimex lectularius); and biological aerosol, including pollen, mold, bacteria, animal dander, fungi, viruses and microbial toxins.

An embodiment of the present disclosure provides a sampling and exposure device to retain trace evidence of bioaerosols and/or arthropod pests for in-situ testing and/or subsequent removal and testing.

An aspect of the present embodiment provides a device having a textile, polymer or cellulose base and a flexible shell for the propagation of an aerosol into an environment.

An aspect of the present embodiment provides a device having a textile polymer or cellulose base and a flexible shell for sampling of tactile microbes and/or bioaerosol within an environment for in-situ examination and/or testing, and/or removal and subsequent examination and/or testing.

An aspect of the present embodiment provides a device having a shell having surface crevices for the differential retention of tactile microbes and settled bioaerosols.

An aspect of the present embodiment provides channels which induce differential settling of bioaerosols entering the device through induced variations in air pressure.

An aspect of the present embodiment provides substantially concentric surface convolutions on the shell for the mitigation of tensile forces across the shell.

An aspect of the present embodiment provides substantially radial surface convolutions on the shell to strengthen the shell.

An aspect of the present embodiment provides a device having one or more coatings to induce differential retention through adhesion by electrostatic force, viscous entrapment, ionic molecular bond, either individually or in combination.

The underside of the shell and/or the floor of the base may be configured to retain evidence of insect and/or bioaerosol presence. For example, the underside of the shell may contain an electrostatic or adhesive coating to physically affix or entrap insects or parts of insects and/or the particulate matter found in bioaerosol. Further alternate chemicals and/or reagents can be affixed to the underside of shell to indicate various environmental conditions upon in-situ visual inspection or subsequent ex-situ processing, inspection or testing. For example, a chemical and/or reagent can be affixed that reacts with oxygen forming an oxide. Analysis of the oxide could provide information regarding the degree of exposure to oxygen; a hygroscopic chemical and/or reagent can be affixed that upon analysis could provide information regarding the degree of humidity; a chemical and/or reagent can be affixed that reacts to temperature changes, which upon analysis could provide information about temperature conditions; or a reagent can be included to detect exposure to one or more genomic alleles indicative of the presence of a pest, allergen or pathogen. All of these measures would provide additional data that could be used individually or in conjunction with other evidence collected in the present embodiment.

An embodiment of the present disclosure provides an arthropod monitoring device comprised of a harborage environment, optionally made from cellulose, polymer, textile or any combination thereof, and a shell affixed to the harborage environment forming a chamber which is capable of active expulsion of an arthropod attractant through differential pressure from one or more forces acting upon that shell. As used herein the term "harborage environment" means a setting perceived by the targeted arthropod, such as, an insect or spider, as a refuge or shelter thereby triggering the harborage seeking behaviors of targeted arthropod to enter the environment.

An embodiment of the present disclosure provides device for detecting arthropods, such as, insects and spider, and bioaerosols comprised of a plurality of units, each unit further comprised of a base and a shell, wherein the shell is affixed to the base to form a chamber and one or more channels where the channel provides access to the chamber.

An embodiment of the present disclosure provides a device for detecting the presence of insects and/or bioaerosols comprising, a base and a shell, where the shell is affixed to the base forming a chamber and at least one channel, the channel provides access to the chamber, the shell can be actuated by a person causing the device to expel air and one or more agents from the chamber to the exterior and to draw in air and/or bioaerosols from the exterior into the chamber.

An aspect of the present embodiment where the agent is an agent having a desired fragrance.

An aspect of the present embodiment where the agent is an agent for attracting certain insects.

An embodiment of the present disclosure provides a device for dispensing an agent comprising, a base and a shell, where the shell is affixed to the base forming a chamber and at least one channel, where the agent is contained in the chamber, the channel provides access to the chamber, the shell can be actuated by a person causing the device to expel air and one or more agents from the chamber to the exterior. As used herein the term "actuated" means manually, or actuated through tactile contact, force or action.

An aspect of the present embodiment where the agent is an agent having a desired fragrance.

An aspect of the present embodiment having one channel.

The present disclosure provides a detection device used for monitoring arthropods, such as insects and spiders, and bioaerosol the device comprising, a base and a shell, wherein the shell is affixed to the base forming a chamber and one or more channels where the channels provide access to the chamber; the shell further comprises a plurality of curved convex surfaces, where each curved convex surface is separated from each adjacent curved convex surface by a crevice; a disc located approximately at the center of the shell; at least one U-joint; and at least one S-joint. As used herein the term "crevice" refers to a nook or recessed space from a surface.

The present disclosure provides a detection device used for monitoring arthropods, such as insects and spiders, and bioaerosol the device comprising, a base and a shell, wherein the shell is affixed to the base forming a chamber and one or more channels where the channels provide access to the chamber, the base further comprises a floor having a plurality of multi-facet supports, each multi-facet support having an outer top facet, an inner top facet, at least one center sloping facet, two sloping channel wall facets, two vertical channel wall facets, two vertical receding channel wall facets, and at least one outward facet, wherein the shell is affixed to the inner top facet. As used herein the term "facet" refers to a substantially flat side of an object having a plurality of sides.

The present disclosure provides a detection device used for monitoring arthropods, such as insects and spiders, and bioaerosol the device comprising, a base and a shell, wherein the shell is affixed to the base forming a chamber and one or more channels where the channels provide access to the chamber; the shell further comprises a plurality of curved convex surfaces, where each curved convex surface is separated from each adjacent curved convex surface by a crevice; a disc located approximately at the center of the shell; at least one U-joint and at least one S-joint; the base further comprises a floor having a plurality of multi-facet supports, each multi-facet support having an outer top facet, an inner top facet, at least one center sloping facet, two sloping channel wall facets, two vertical channel wall facets, two vertical receding channel wall facets, and at least one outward facet, wherein the shell is affixed to the inner top facet.

An aspect of the present embodiment having one or more channels, where the channels may have the same dimensions and configurations or alternatively, channels within the same device may have different dimensions and configurations. Channels may be configured to form multiple chambers. The multiple chambers may include in one or more of the internal features, such as a medium that would through degradation, oxidation, dessication or other reaction indicate the duration, volume or other attributes of the devices exposure, thereby providing additional context for interpreting accrued evidence of bioaerosols and/or arthropod.

An aspect of the present disclosure provides a base constructed from a combination of a non-woven biologically inert polymer and a stiffening polymer. The stiffening polymer is added to the non-woven biologically inert polymer during manufacture. For example, the stiffening polymer can be injected into the non-woven biologically inert polymer while the non-woven biologically inert polymer is embossed in a compound hot embossing die. The present embodiment provides a material for the base that is very stiff, while still being highly permeable. These characteristics facilitate the detection for desired pests and bioaerosols. For example, suitable reagents can be flushed into the chamber, the reagents entering through the channels and exiting through the base made from a permeable material. A reagent is selected having the physical characteristic of being able to dissolve targeted agents that are indicative of the presence of targeted pests and targeted bioaerosols. The recovered reagent can then be tested for the presence of the targeted agents. An aspect of the present embodiment provides a device having a shell made from a form resilient material. As used herein the term "form resilient" or "form resilience" refers to the quality where a material can deform when a force is applied to it, and then return to its original position when the force is removed. The shell made from form resilient material of the present disclosure provides a flexible structure whose supporting attachments are exclusively upon its periphery so as to enable and encourage flexure when acted upon by a force. When the external force is removed, the flexure of such a structure would rebound due to tensile forces inherent in the material.

An aspect of the present embodiment provides a device where the underside of the base is coated with a contact adhesive, or has a magnet, hook and loop, that is, Velcro® or other structure for holding the device against a horizontal, inclined, vertical or inverted surface.

The channel(s) may have dimensions (cross-section, depth and height) and configurations (shape of channel) that vary to facilitate various desired effects. For example, the channel(s) may be configured to attract and retain certain thigmotropic insects. Channel(s) may be straight radial to the center of the device; may be compound-contoured, for example in a serpentine pattern; may be spiral; or any combination thereof. Channel(s) may be consistent in cross-section dimension, or the cross-section may be varied to increase thigmotropism thereby attracting and trapping targeted insects; or to alter the flow of air carrying particulates thereby depositing the particulates at desired location(s) in the interior space of the device. Channel(s) may be configured having lateral and/or vertical protuberances, such as a flair configuration, that cause disruption of flow rate facilitating a desired differential pattern of particulate settling. Similarly channel(s) may have a valve configuration that causes a desired directional of air flow thereby facilitating the capture or entanglement of targeted insects. In embodiments where there are one or more channels, the channels may have the same dimensions and configurations or alternatively, channels within the same device may have different dimensions and configurations. Channels may be configured to form multiple chambers. The multiple chambers may include in one or more of the internal features, such as a medium that would through degradation, oxidization, dessication or other reaction indicate the duration, volume or other attributes of the devices exposure, thereby providing additional context for the interpretation of bioaerosols and/or arthropod evidence accrued.

The shell may be made from polymer, elastomer or thermoplastic. The shell may be made from a single layer of material, or it may be made from several layers of material laminated together. Alternatively the laminated layers may not be in direct contact with the adjacent laminated layer forming intervening air gaps in the shell. The shell can be opaque, translucent or transparent. An aspect of this embodiment provides a shell made from transparent material where print or graphical information can be printed on the inner side that can be viewed from the outside. This configuration prevents scuffling or other effects of use from degrading the outward appearance, and also preserves the legibility of the printed and/or graphical information. The shell may be flexible or rigid.

The shell may be affixed to any of the top facets, that is, the inner top facet or the out top facet. Alternately the shell can be secured without having a vertical abutment facet. The inner top and out top facets may be set at any angle from 0 to 45 degrees relative to base of the device.

The ratio of the depth of the device to the width of the device can range from about 0.25 to 1; 0.3 to 1; 0.4 to 1; 0.5 to 1 0.6 to 1; and 0.7 to 1. The ratio of the width of the device to the length of the device can range from about 1 to 1 (a substantially circular shape); 1 to 1.2; 1 to 1.3; 1 to 1.4; 1 to 1.5; 1 to 1.6; 1 to 1.7; 1 to 1.8; 1 to 1.9; 1 to 2; 1 to 3; 1 to 4; 1 to 5; or 1 to 6. The dimensions of the disclosed embodiments can be varied to either increase or decrease the amount of air that sampled; and to optimize targeted insects or bioaerosols.

When the shell is depressed, the air in the chamber is forced from a larger volume to a smaller volume providing an increase in air pressure to expel the air and any materials, such as fragrances and chemical lures from the chamber to the exterior of the device. When the shell returns to it normal state, the volume of chamber increases returning to its normal volume resulting in a decrease in air pressure. Air is drawn into the chamber. The force of the air entering through the channels decreases gradually as the volume of space available to the air increases from the space available in the channels to the increased space in the interior of the device due to the combination of the increased height of the shell and the orientation of the facets of the multi-facet supports effectively widening the walls of the channels. This effect enhances the differential settling of any materials carried by the inward air flow. The action of the shell is manually actuated through human "tapping", as well as through resonance after physical contact such as rustling, resonance from sounds, and through normal tidal air flow and gusting.

The outer surface of the shell provides a detection surface from bioaerosol settling from air, arthropods crawling, and from tactile contact with human hands, such as when a human taps the shell during manual actuation.

The underside of the shell and/or the floor of the base may be configured to retain evidence of insect and/or bioaerosol presence. For example, the underside of the shell may contain an electrostatic or adhesive coating to physically affix insects and/or the particulate matter found in bioaerosol. Further alternate chemicals and/or reagents can be affixed to the underside of shell to indicate various environmental conditions. For example, a chemical and/or reagent can be affixed that reacts with oxygen forming an oxide. Analysis of the oxide could provide information regarding the degree of exposure to oxygen; a hygroscopic chemical and/or reagent can be affixed that upon analysis could provide information regarding the degree of humidity; a chemical and/or reagent can be affixed that reacts to temperature changes, which upon analysis could provide information about temperature conditions. All of these measures would provide additional data that could be used individually or in conjunction with other evidence collected in the present embodiment.

FIG. 1 provides a side plane view of an embodiment of the present disclosure, an insect and bioaerosol detection device 100 having a widthwise dimension extending in the D2 direction and depth dimension extending in the D3 direction. The D3 direction is understood as moving from a top to bottom direction, or alternatively, an up to down direction. The device 100 having a base 102 and a shell 104. The base 102 is attached to the shell 104 forming a chamber 106, and one or more channels (not shown) that can provide access to the chamber from the exterior of the device 100. The base 102 may be constructed from cellulosic materials, such as paper, elastomers, thermoplastics, woven or non-woven textiles or any combination thereof.

Figure 2:
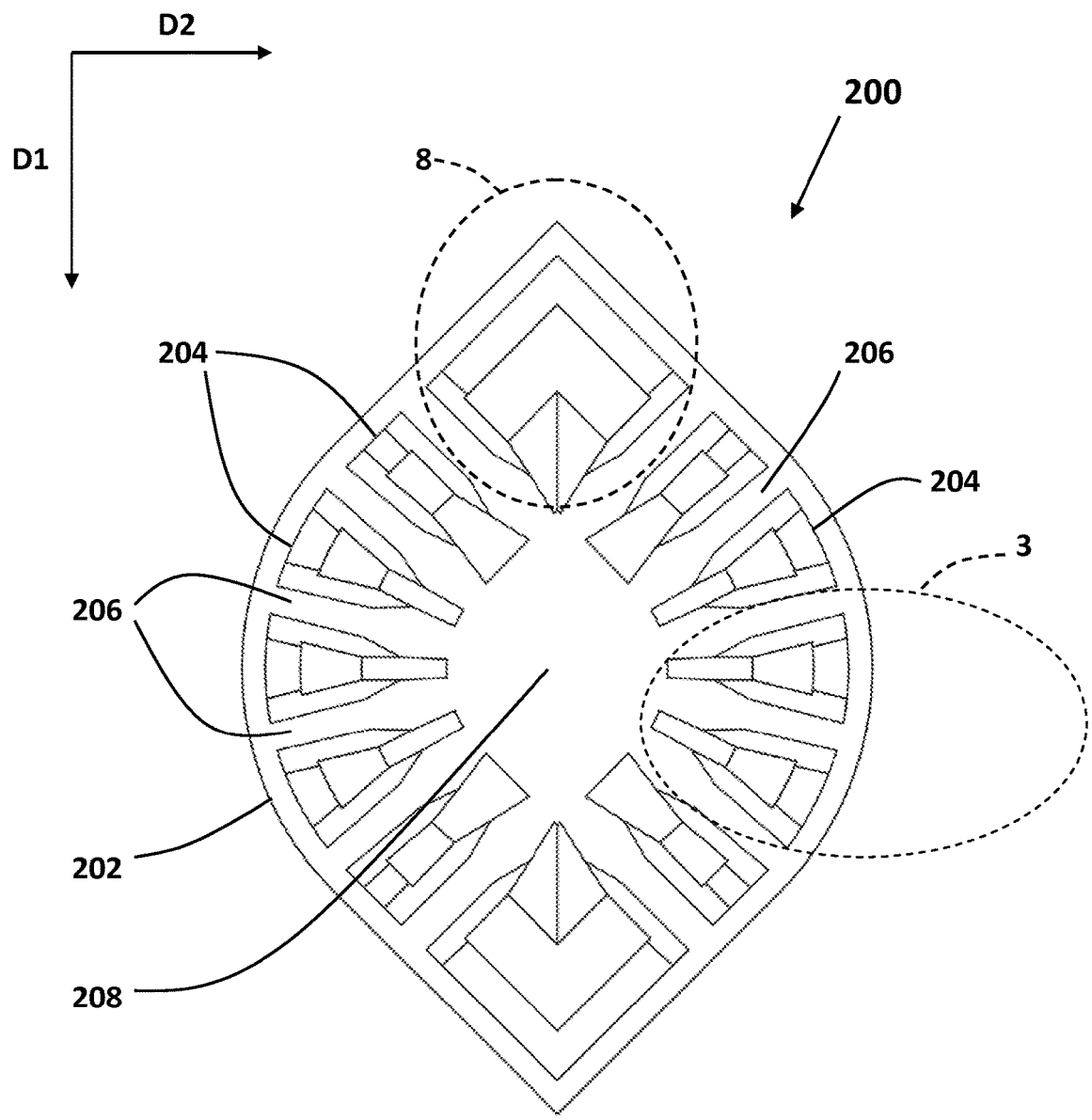
FIG. 2 depicts a base of an insect and bioaerosol detection device of the present disclosure.
Figure 8:
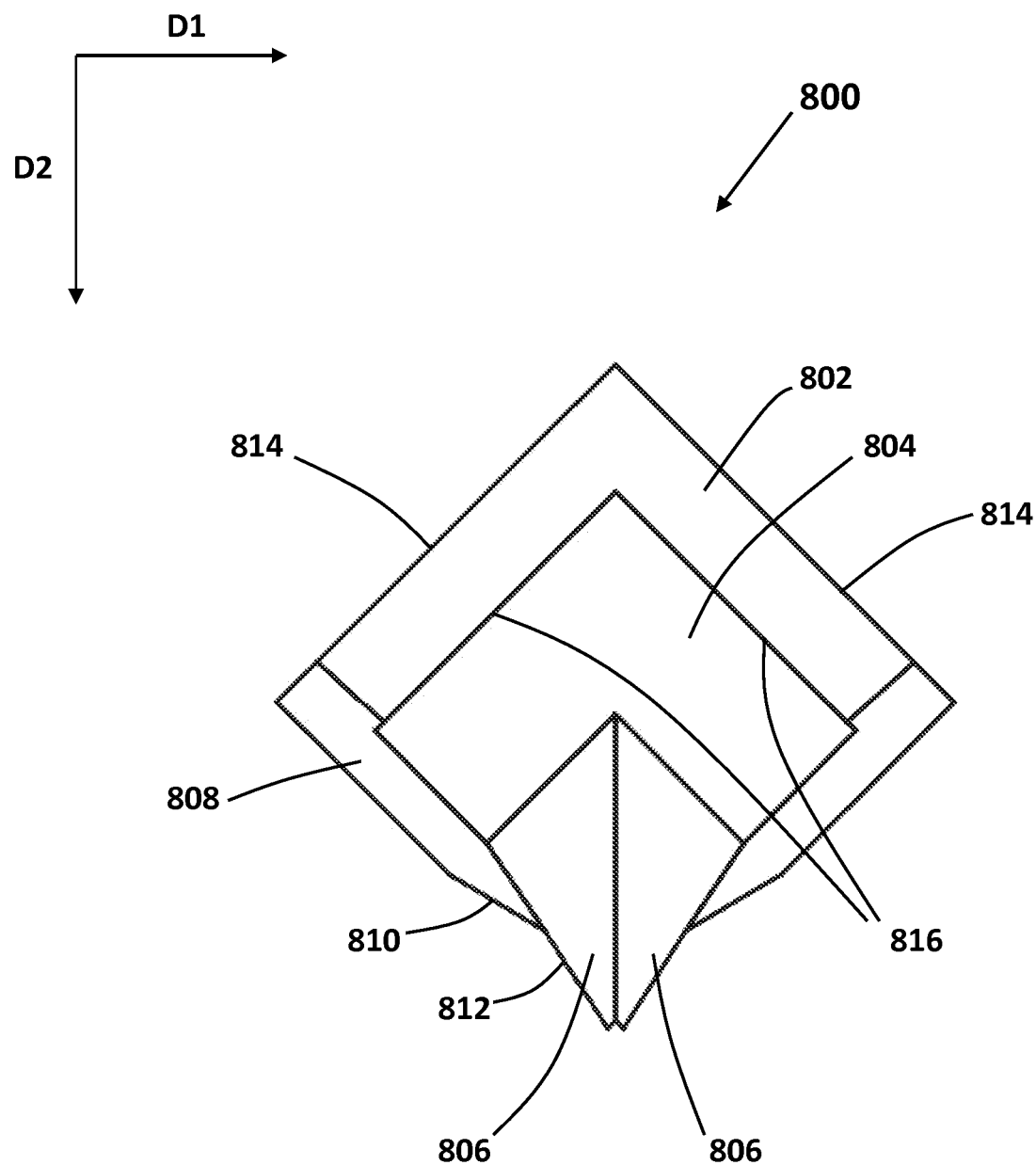
FIG. 8 depicts an alternate multi-facet support referenced in FIG. 2.
Figure 9:
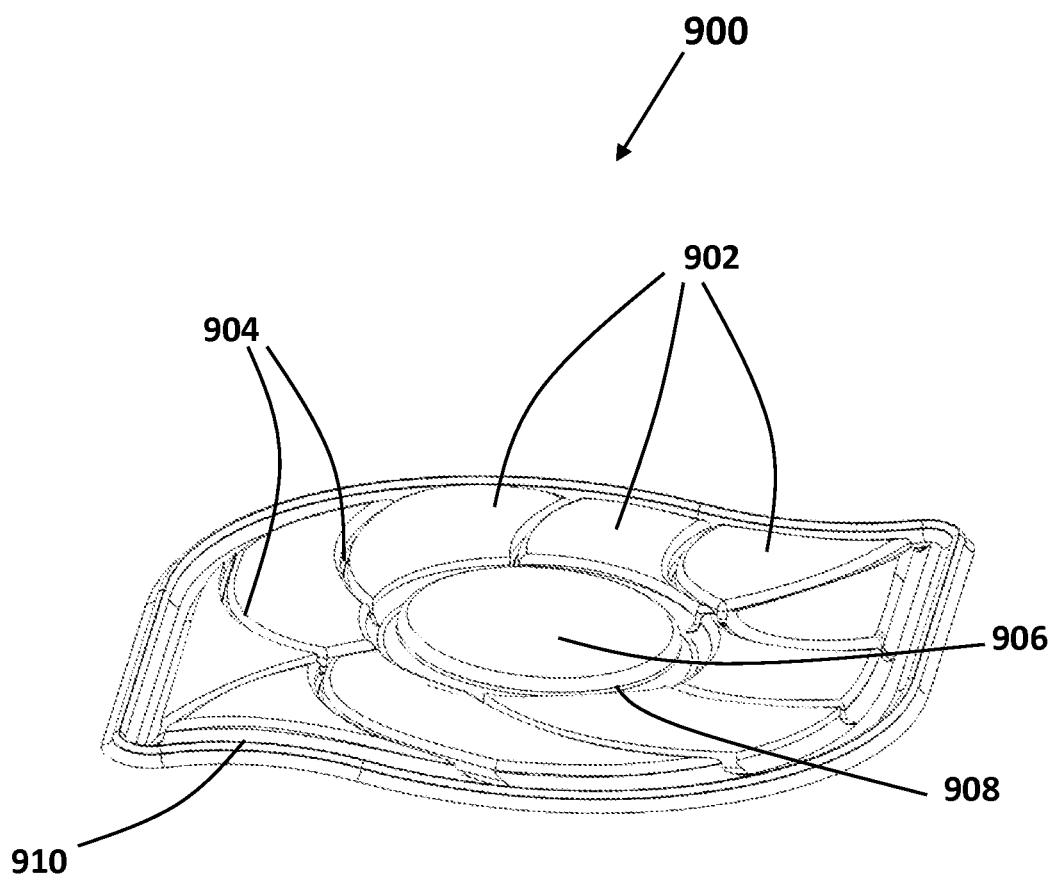
FIG. 9 depicts a shell of an embodiment of the present disclosure.
Figure 10:
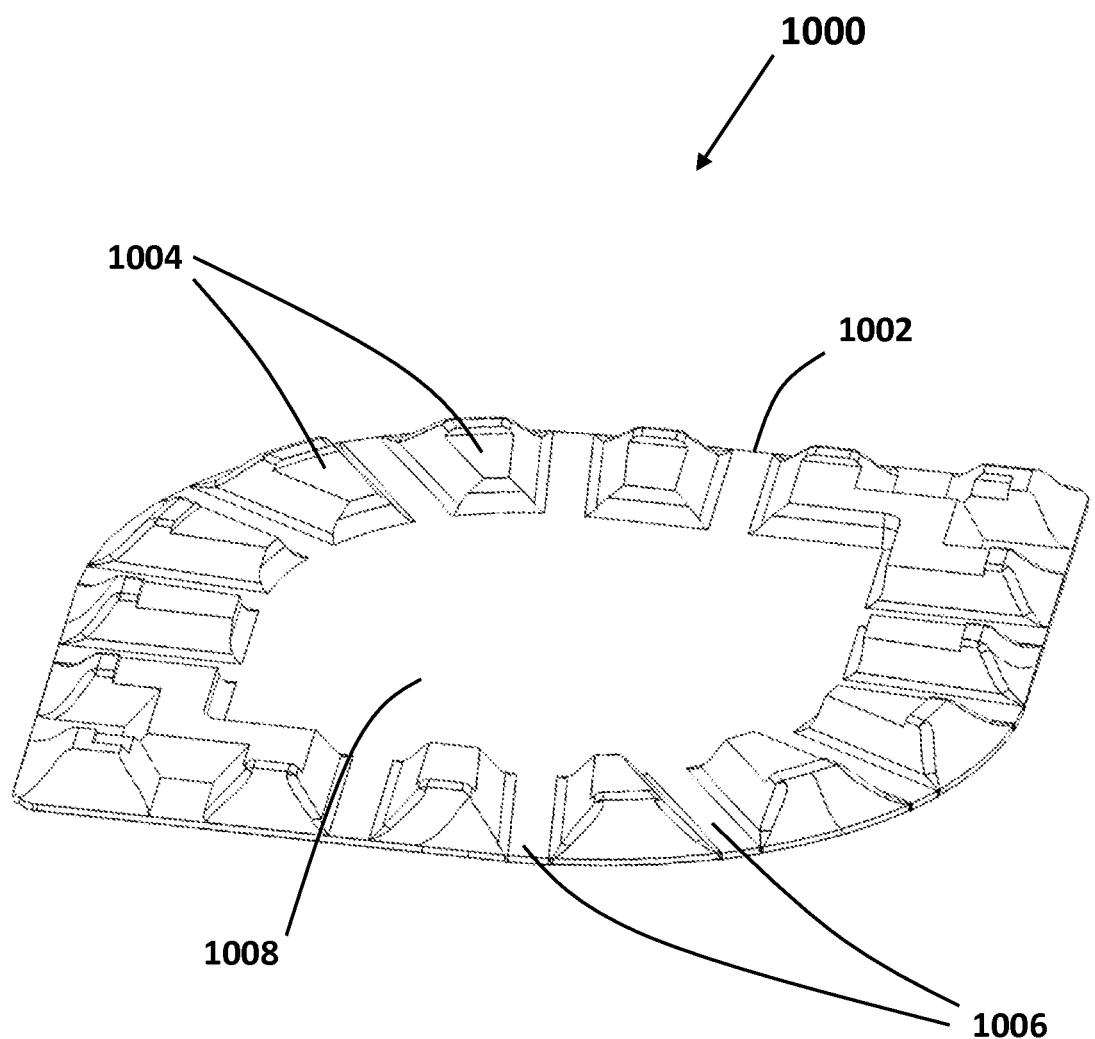
FIG. 10 depicts a base of an embodiment of the present disclosure.
Figure 11:
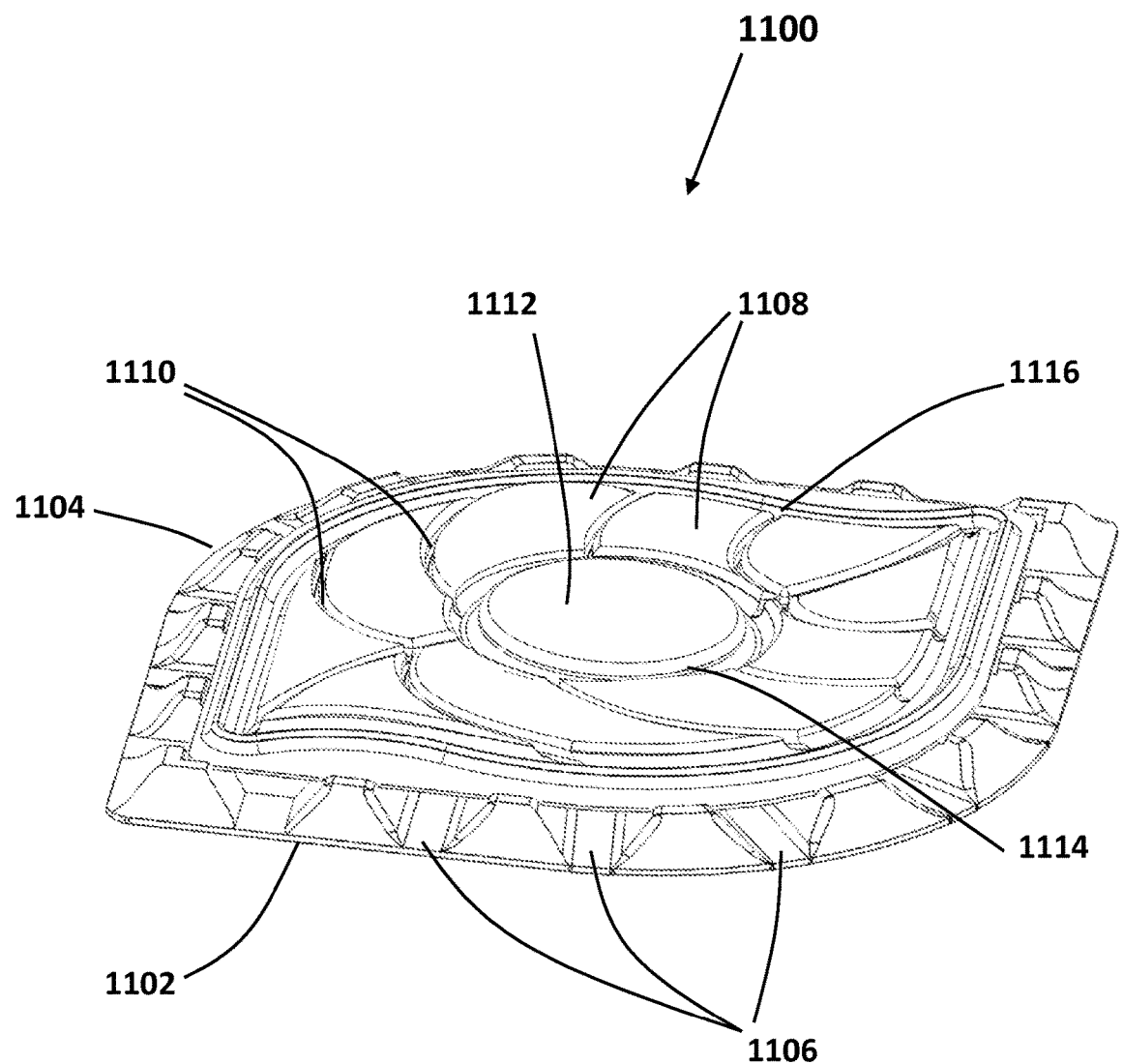
FIG. 11 depicts a detection device used for monitoring arthropods, such as insects and spiders, and bioaerosol of the present disclosure.
Figure 12:
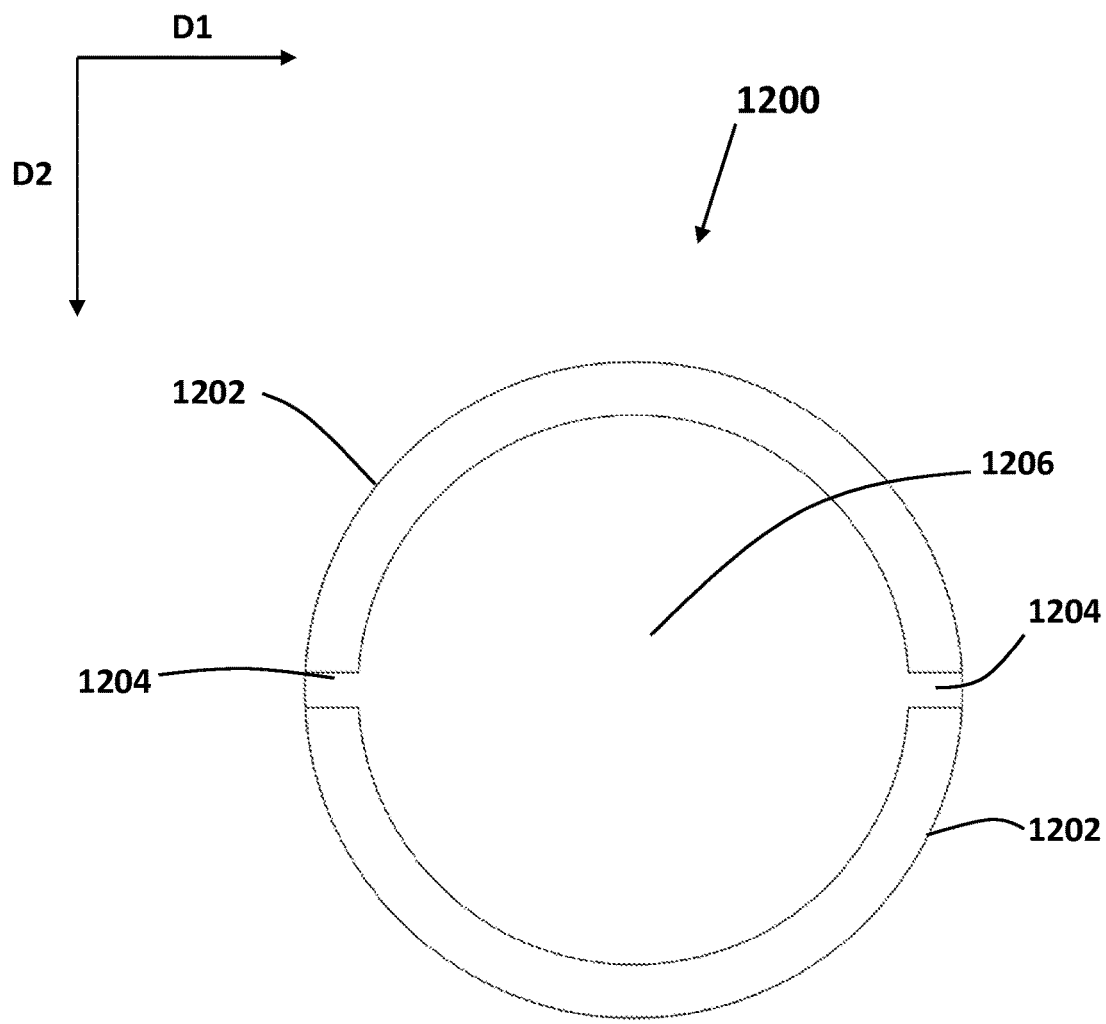
FIG. 12 depicts a base of a device for detecting the presence of insects and bioaerosols.
Figure 13:
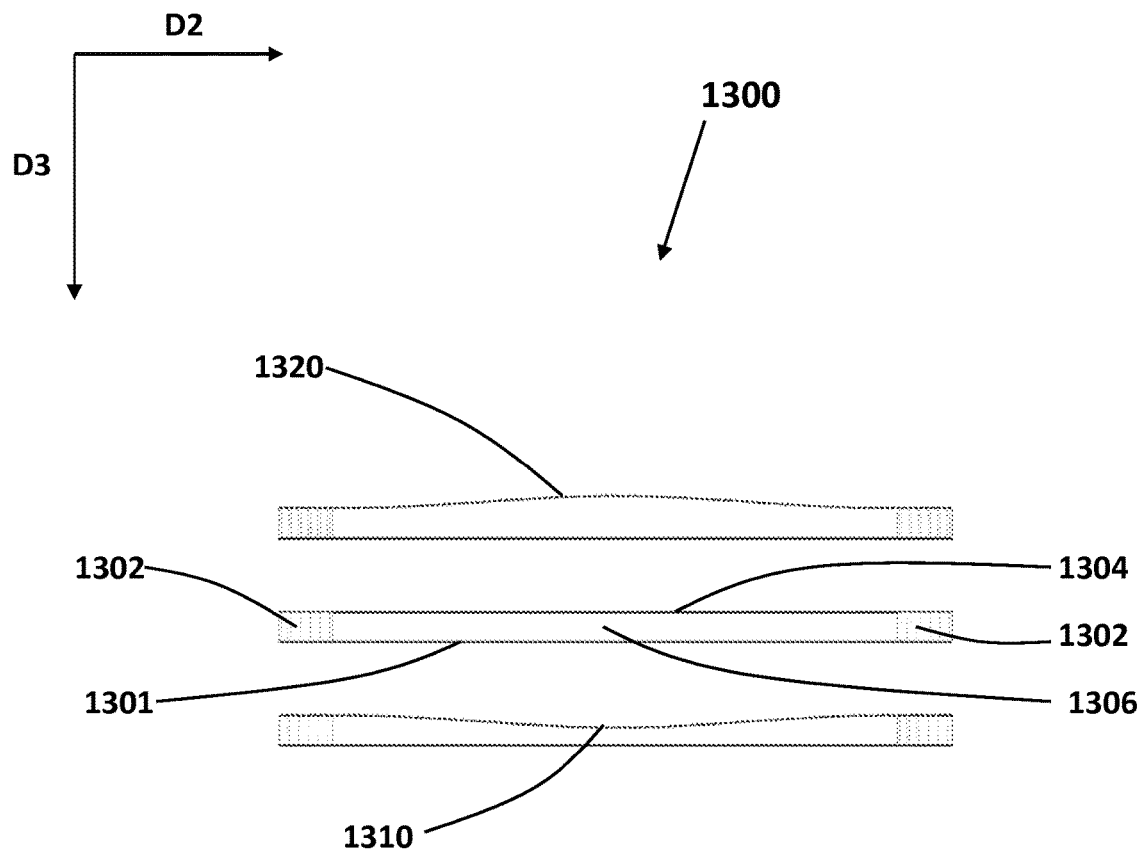
FIG. 13 depicts an embodiment of the present disclosure, an insect and/or bioaerosol detection device.

FIG. 2 provides a top down view of a base 200 of an insect and bioaerosol detection device having a width wise dimension extending in the D2 direction and a lengthwise dimension extending in the D1 direction. The base comprises a floor 202 having a plurality of multi-facet supports 204. The multi-facet supports are positioned to form the walls of a plurality of channels 206 that provide access to the chamber 208 that is formed when the shell (not shown) is affixed to the base 200 through the multi-facet supports. An enlargement of two multi-facet supports is provided in FIG. 3. An enlargement of an alternate multi-facet support is provided in FIG. 8.

Figure 3:
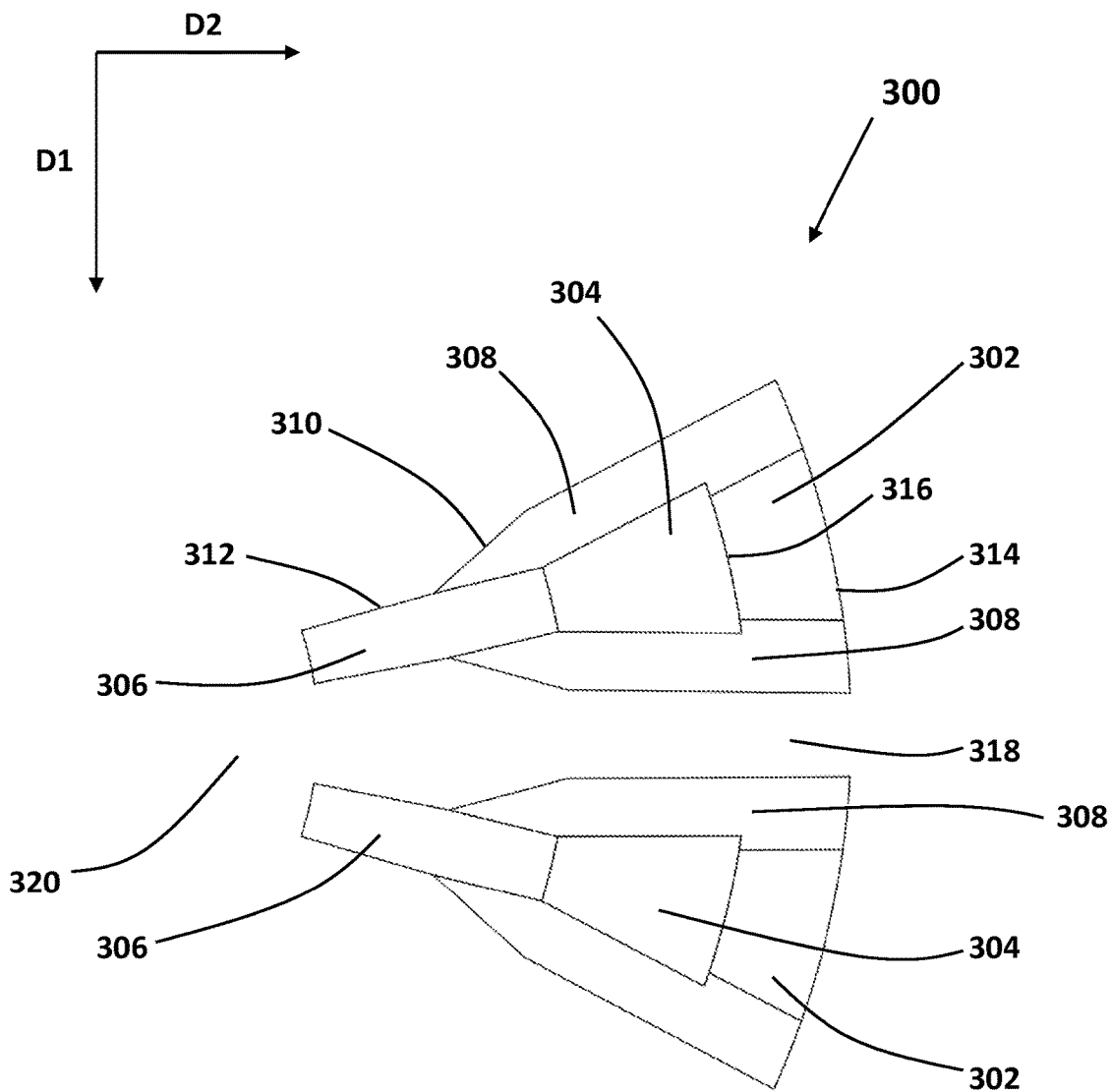
FIG. 3 depicts an enlarged top down perspective of the multi-facet supports referenced in FIG. 2.

FIG. 3 provides an enlarged top down view of the multi-facet supports referenced in FIG. 2. A multi-facet support is comprised of a plurality of top, vertical and sloping facets. Depending on the perspective of the figure, certain facets because of their orientation will appear as flat planes, while others will appear as lines. For example in the present figure, the top facets and sloping facets appear as flat planes. The vertical facets appear as lines since they are being viewed edgewise. A multi-facet support 300 comprises an outer top facet 302, an inner top facet 304, one or more center sloping facets 306, and two sloping channel wall facets 308, two vertical receding channel wall facets 310 (seen edgewise from this perspective), two vertical channel wall facets 312 (seen edgewise from this perspective) and one or more outward facet 314 (seen edgewise from this perspective). The shell (not shown) is affixed to the inner top facet 304. The outward facet 314 forms the external side of the multi-facet support 300. The inner top facet 304 and the outer top facet 302 form a vertical abutment facet 316 (seen edgewise from this perspective) that the edge of the shell abuts against. The sloping channel wall facets 308 of adjacent multi-facet supports forms the wall of a channel 318 that is formed by the aforementioned two adjacent multi-facet supports. The channel 318 provides access to the chamber 320.

Figure 4:
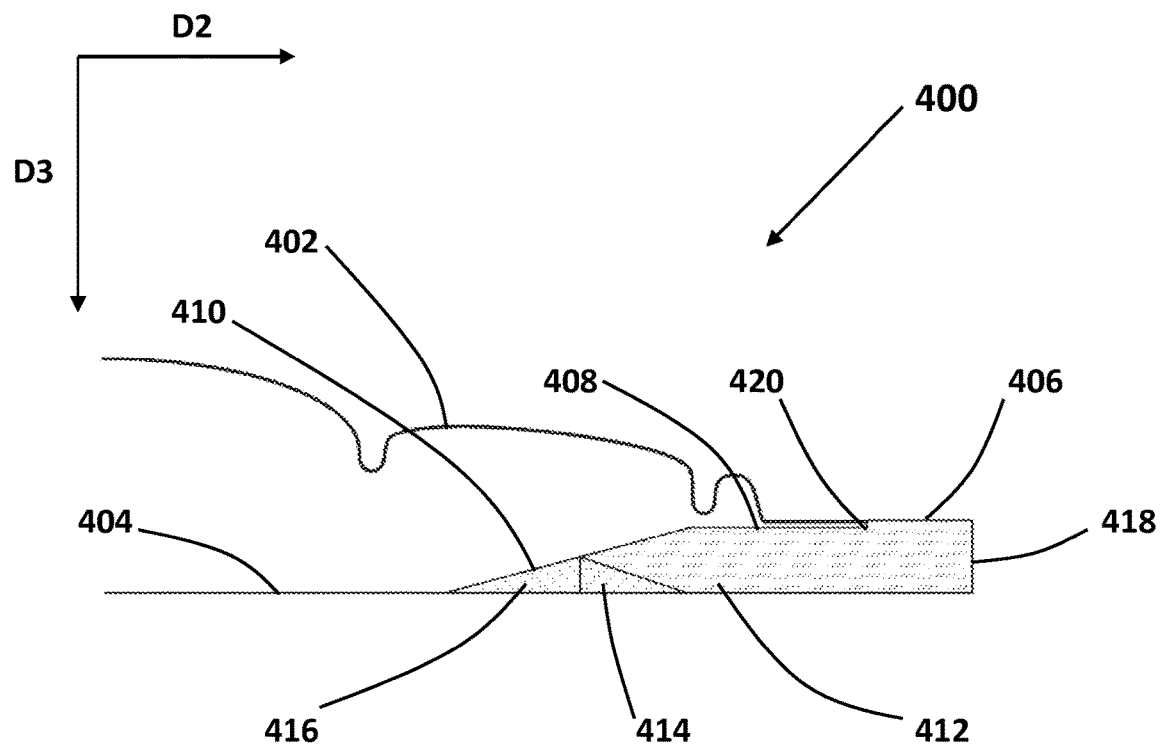
FIG. 4 depicts an embodiment of a multi-facet support.

FIG. 4 provides a side view of an embodiment of a multi-facet support 400 relative to the D2 direction and D3 direction. A multi-facet support is comprised of a plurality of top, vertical and sloping facets. Depending on the perspective of the figure certain facets because of their orientation will appear as flat planes, while others will appear as lines. The present figure provides a shell 402, the floor of the base 404, an outer top facet 406 (seen edgewise from this perspective), an inner top facet 408 (seen edgewise from this perspective), a center sloping facet 410 (seen edgewise from this perspective), and a sloping channel wall facet 412, a vertical receding channel wall facets 414, a vertical channel wall facets 416, an outward facet 418 (seen edgewise from this perspective), and a vertical abutment facet 420 (seen edgewise from this perspective). The shell 402 is affixed to the inner top facet 408 where the edge of the shell abuts against the vertical abutment facet 416.

Figure 5:
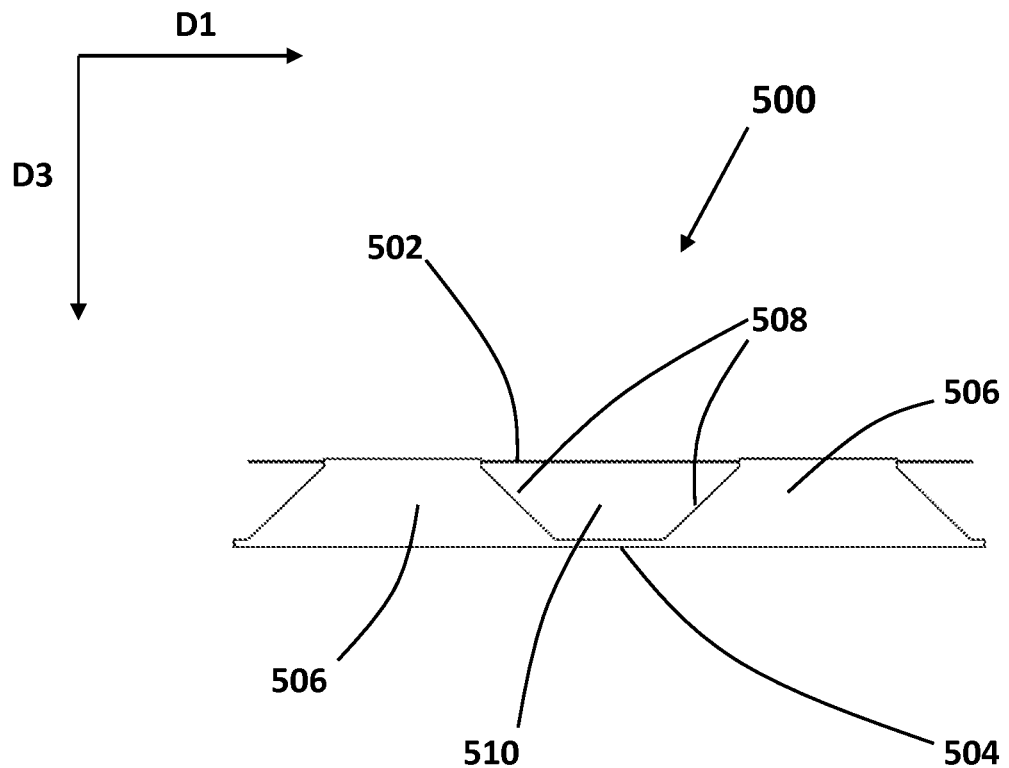
FIG. 5 depicts two multi-facet supports.

FIG. 5 provides a side view of two multi-facet supports 500 according to the D1 direction and D3 direction having the vantage point of viewing the multi-facet supports from the exterior to the interior of the device. The present figure provides the shell 502, the floor of the base 504, the outward facets of two adjacent multi-facet supports 506, the sloping channel wall facets of the two adjacent multi-facet supports 508 (seen edgewise from this perspective) and the channel 510 formed by the two adjacent multi-facet supports.

Figure 6:
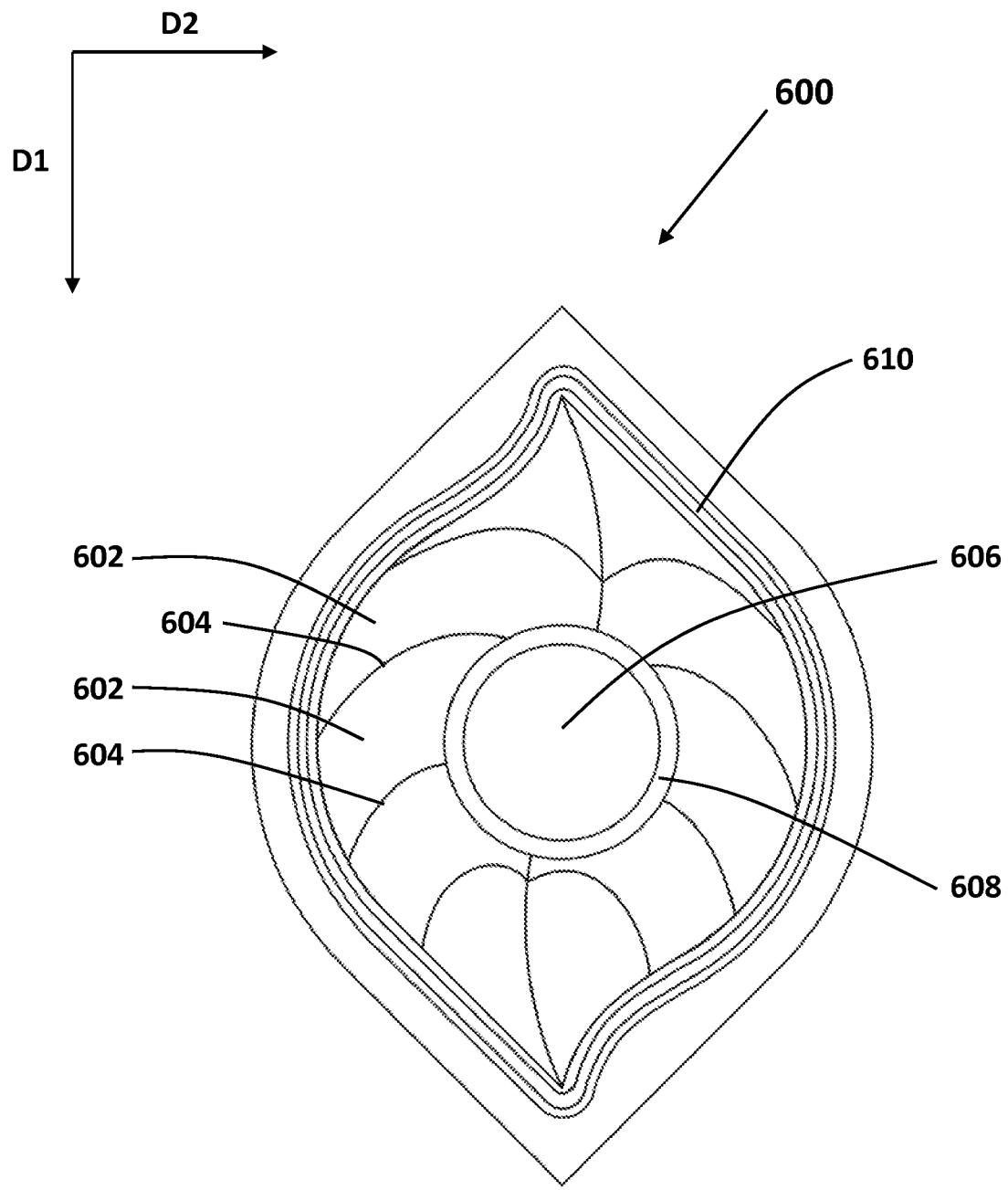
FIG. 6 depicts a shell of an insect and bioaerosol detection device of the present disclosure.
Figure 7:
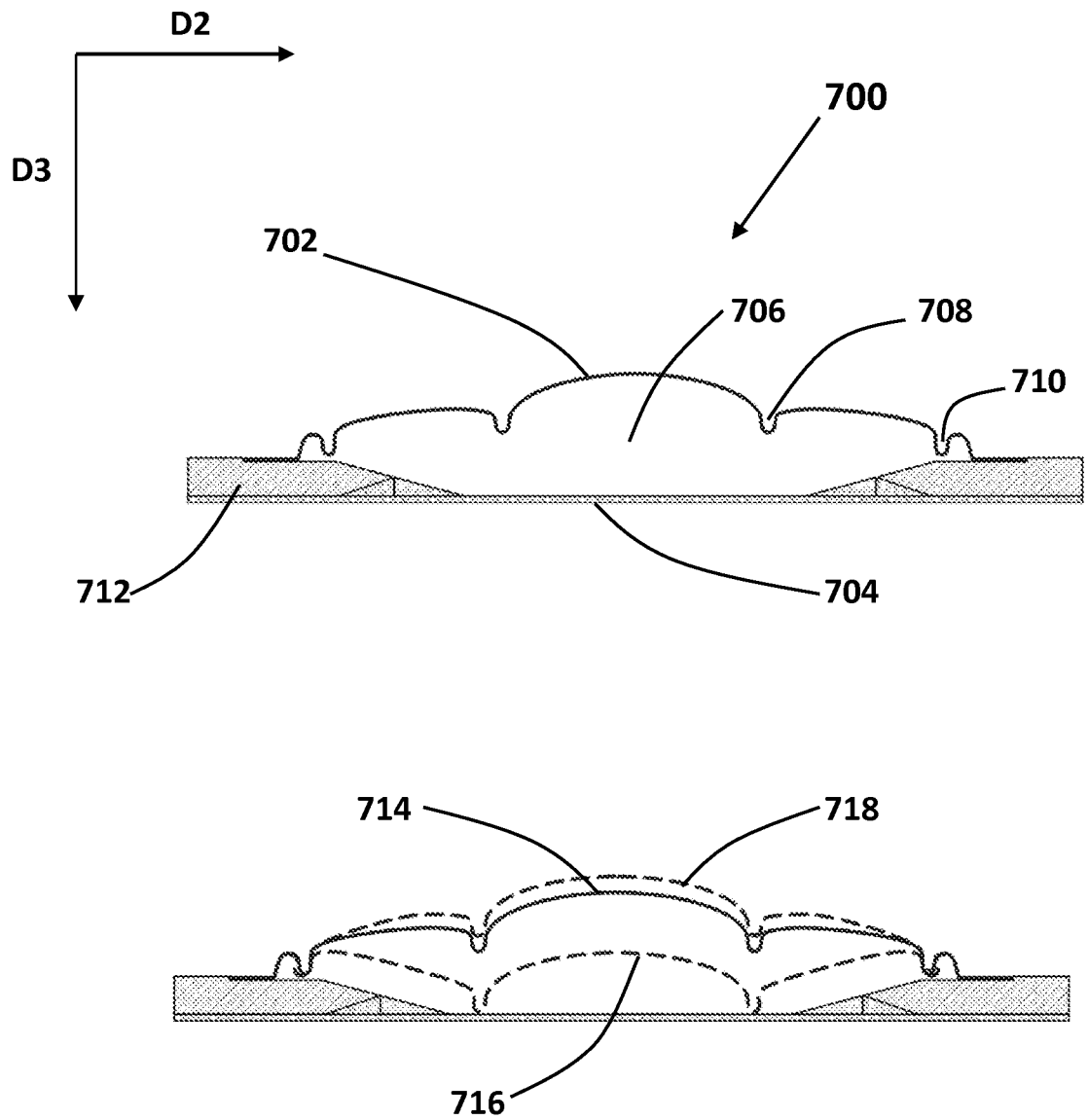
FIG. 7 depicts an embodiment of an insect and bioaerosol detection device of the present disclosure.

FIG. 6 provides a top down plane view of a shell 600 of an insect and bioaerosol detection device having a width wise dimension extending in the D2 direction and a lengthwise dimension extending in the D1 direction. The shell has a plurality of curved convex surfaces 602, where each curved convex surface is separated from each adjacent curved convex surface by a crevice 604. The curved convex surfaces are arranged around a disc 606 that is located approximately at the center of the shell. The shell includes at least one U-joint 608 and at least one S-joint 610.

FIG. 7 provides a side plane view of an embodiment of the present disclosure, an insect and bioaerosol detection device 700 having a widthwise dimension extending in the D2 direction and depth dimension extending in the D3 direction. The D3 direction is understood as moving from a top to bottom, or alternatively, an up to down direction. The device 700 having a base 704 and a shell 702. The shell 702 is attached to the base 704 forming a chamber 706, and one or more channels (not shown) that can provide access to the chamber from the exterior of the device 700. The shell includes at least one U-joint 708 and at least one S-joint 710. Solid line 714 shows the original position of the shell 702. Phantom line 716 shows the position of the shell 702 when downward force is applied to the shell 702 expelling air and materials from the chamber 706. Phantom line 718 shows the upward position the shell 702 moves to when the downward force is removed. Upon removal of the downward force, the shell 702 returns to its original position 714.

The U-joint 708 and S-joint 710 in combination with the material that the shell 702 is made from, facilitate the bending of the shell when the downward force is applied to depress it down to expel air and materials from the chamber; and upon removal of the downward force, returns the shell 702 upward past its original position before the shell 702 returns to its original position.

FIG. 8 provides an enlarged top down view of an alternate multi-facet support referenced in FIG. 2. A multi-facet support is comprised of a plurality of top, vertical and sloping facets. Depending on the perspective of the figure, certain facets because of their orientation will appear as flat planes, while others will appear as lines. For example in the present figure, the top facets and sloping facets appear as flat planes. The vertical facets appear as lines since they are being viewed edgewise. A multi-facet support 800 comprises an outer top facet 802, an inner top facet 804, two center sloping facets 806, and two sloping channel wall facets 808, two vertical receding channel wall facets 810 (seen edgewise from this perspective), two vertical channel wall facets 812 (seen edgewise from this perspective) and two outward facets 814 (seen edgewise from this perspective). The shell (not shown) is affixed to the inner top facet 804. The outward facets 814 forms the external side of the multi-facet support 800. The inner top facet 804 and the outer top facet 802 form two vertical abutment facets 816 (seen edgewise from this perspective) that the edge of the shell abuts against. The sloping channel wall facets 808 of adjacent multi-facet supports forms the wall of a channel 818 that is formed with the adjacent multi-facet supports (not shown).

FIG. 9 provides a perspective view of a shell 900 of an embodiment of the present disclosure. The shell has a plurality of curved convex surfaces 902, where each curved convex surface is separated from each adjacent curved convex surface by a crevice 904. The curved convex surfaces are arranged around a disc 906 that is located approximately at the center of the shell. The shell includes at least one U-joint 908 and at least one S-joint 910.

FIG. 10 provides a perspective view of a base 1000 of an embodiment of the present disclosure. The base comprises a floor 1002 having a plurality of multi-facet supports 1004. The multi-facet supports are positioned to form the walls of a plurality of channels 1006 that provide access to the chamber 1008 that is formed when the shell (not shown) is affixed to the base 1000 via the multi-facet supports.

FIG. 11 provides a perspective view of a detection device 1100 used for monitoring arthropods, such as insects and spiders, and bioaerosol. The device having a base 1102 and a shell 1104, wherein the shell is affixed to the base forming a chamber (not shown) and a plurality of channels 1106 where the channels provide access to the chamber. The shell having a plurality of curved convex surfaces 1108, where each curved convex surface is separated from each adjacent curved convex surface by a crevice 1110; a disc 1112 located approximately at the center of the shell; at least one U-joint 1114; and at least one S-joint 1116.

FIG. 12 provides a top down view of the base 1200 of a device for detecting the presence of insects and bioaerosols. The base having one or more supports 1202 upon which the shell (not shown) is affixed, and having two channels 1204 that provide access to the chamber 1206.

FIG. 13 provides a side plane view of an embodiment of the present disclosure, an insect and/or bioaerosol device 1300 having a widthwise dimension extending in the D2 direction and depth dimension extending in the D3 direction. The D3 direction is understood as moving from a top to bottom, or alternatively, an up to down direction. The base 1301 is embossed from a single material. The base having one or more supports 1302 upon which the shell 1304 is affixed, and at least one channel (not shown) that provides access to the chamber 1306. Phantom line 1310 shows the position of the shell 1304 when downward force is applied to the shell 1304 expelling air and materials from the chamber 1306. Phantom line 1320 shows the upward position the shell 1304 moves to when the downward force is removed. Upon removal of the downward force, the shell 1306 returns to its original position.

Figure 14:
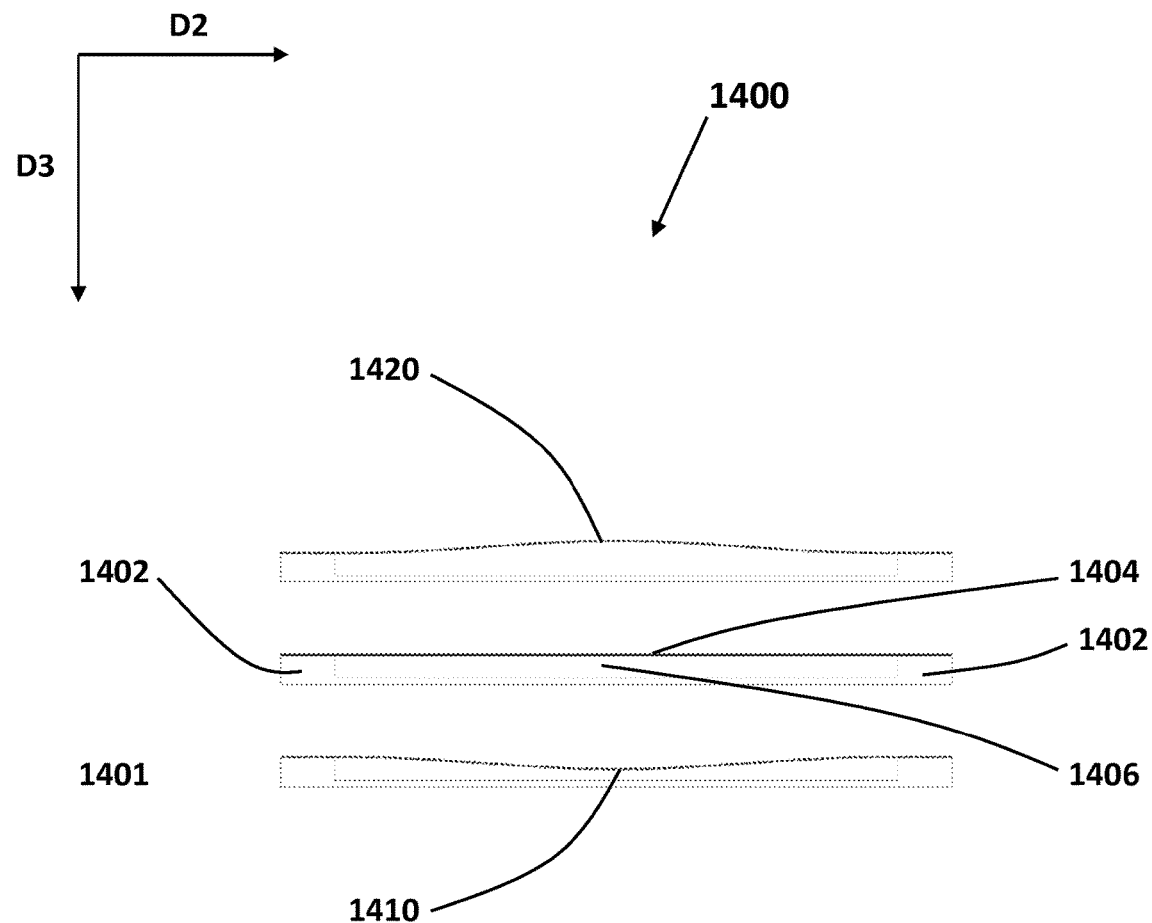
FIG. 14 depicts an embodiment of the present disclosure, an insect and/or bioaerosol detection device.

FIG. 14 provides a side plane view of an embodiment of the present disclosure, an insect and/or bioaerosol device 1400 having a widthwise dimension extending in the D2 direction and depth dimension extending in the D3 direction. The D3 direction is understood as moving from a top to bottom, or alternatively, an up to down direction. The base 1401 is made from a plurality of laminated, that is, glued materials. The base having one or more supports 1402 upon which the shell 1404 is affixed, and at least one channel (not shown) that provides access to the chamber 1406. Phantom line 1410 shows the position of the shell 1404 when downward force is applied to the shell 1404 expelling air and materials from the chamber 1406. Phantom line 1420 shows the upward position the shell 1404 moves to when the downward force is removed. Upon removal of the downward force, the shell 1406 returns to its original position.

Figure 15:
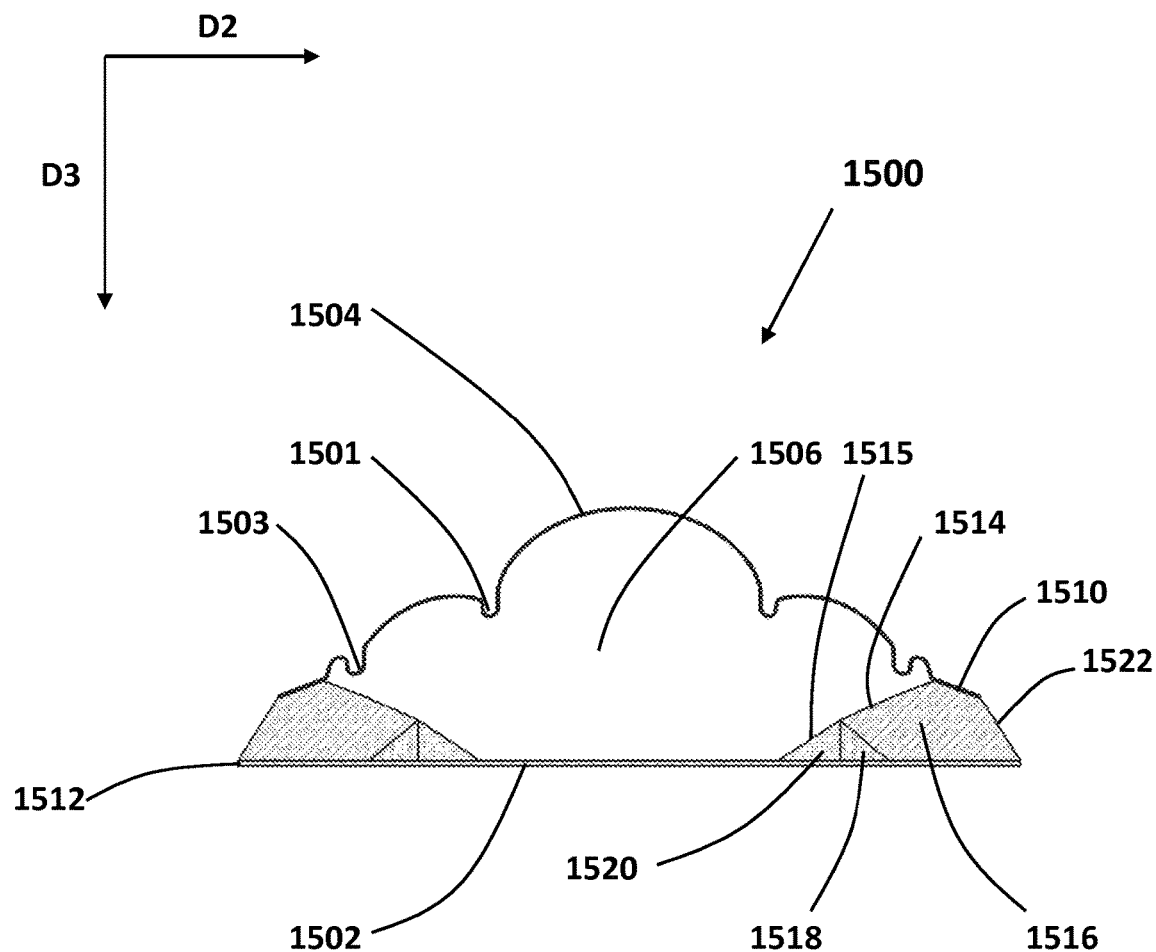
FIG. 15 depicts an embodiment of the present disclosure.

FIG. 15 provides a side plane view of an embodiment of the present disclosure, an insect and bioaerosol detection device 1500 having a widthwise dimension extending in the D2 direction and depth dimension extending in the D3 direction. The D3 direction is understood as moving from a top to bottom direction, or alternatively, an up to down direction. The device 1500 having a base 1502 and a shell 1504. The shell 1504 is attached to the base 1502 forming a chamber 1506, and one or more channels (not shown) that can provide access to the chamber from the exterior of the device 1500. The shell having a U-joint 1501 and a S-joint 1503. In the present illustrated embodiment the shell 1504 is affixed to a outer top facet 1510 (seen edgewise from this perspective) of a multi-facet support 1512. The multi-facet support 1512 having a inner top facet 1514 (seen edgewise from this perspective), a center sloping facet 1515 (seen edgewise from this perspective), a sloping channel wall facet 1516, a vertical receding wall facet 1518, a vertical channel wall facet 1520, and a outward facet 1522 (seen edgewise from this perspective).

While the present invention has been illustrated and described herein in terms of an embodiment and several alternatives, it is to be understood that the techniques described herein can have a multitude of additional uses and applications. Accordingly, the invention should not be limited to just the particular description and various drawing figures contained in this specification that merely illustrate a preferred embodiment and application of the principles of the invention.

What is claimed is:

1. A detection device used for monitoring arthropods and/or bioaerosol said device comprising, a base and a shell, wherein said shell is affixed to said base forming a chamber and one or more channels where said channels provide access to said chamber; said shell further comprises a plurality of curved convex surfaces, where each curved convex surface is separated from each adjacent curved convex surface by a crevice; a disc located approximately at the center of the shell; at least one U-joint; and at least one S joint.

2. The device of claim 1 wherein said agent is an agent having a desired fragrance.

3. The device of claim 1 wherein said agent is an agent for attracting certain insects.

4. The device of claim 1 having one channel.

5. A detection device used for monitoring arthropods and/or bioaerosol said device comprising, a base and a shell, wherein said shell is affixed to said base forming a chamber and one or more channels where said channels provide access to said chamber, said base further comprises a floor having a plurality of multi-facet supports, each multi-facet support having an outer top facet, an inner top facet, at least one center sloping facet, two sloping channel wall facets, two vertical channel wall facets, two vertical receding channel wall facets, and at least one outward facet, wherein said shell is affixed to said inner top facet.

6. The device of claim 5 wherein said agent is an agent having a desired fragrance.

7. The device of claim 5 wherein said agent is an agent for attracting certain insects.

8. The device of claim 5 having one channel.

* * * * *